ns Patent [19]

Schulenberg et al.

[11] Patent Number: 4,984,576
[45] Date of Patent: Jan. 15, 1991

[54] CIRCUITRY FOR HEARTBEAT

[75] Inventors: Andreas Schulenberg, Schönaich; Martin Schraag, Sindelfingen, both of Fed. Rep. of Germany

[73] Assignee: Hewlett-Packard Company, Palo Alto, Calif.

[21] Appl. No.: 431,723

[22] Filed: Nov. 2, 1989

Related U.S. Application Data

[63] Continuation of Ser. No. 148,205, Jan. 19, 1988, abandoned, which is a continuation of Ser. No. 85,267, Aug. 11, 1987, abandoned, which is a continuation of Ser. No. 867,346, May 23, 1986, abandoned.

[30] Foreign Application Priority Data

May 25, 1985 [DE] Fed. Rep. of Germany ....... 3518967

[51] Int. Cl.$^5$ ............................................. A61B 8/02
[52] U.S. Cl. .................................................. 128/661.07
[58] Field of Search ........................................ 148/205

[56] References Cited

U.S. PATENT DOCUMENTS 3,561,430 2/1971 Filler, Jr. et al. .................... 128/661

OTHER PUBLICATIONS

Rapoport et al., "A pilot clinical pep monitor", IEEE Transactions on Biomedical Eng. vol. BME-26, No. 6, Jun. 1979, pp. 345–349.

Primary Examiner—Francis Jaworski
Attorney, Agent, or Firm—Frank R. Perillo

[57] ABSTRACT

A circuit for heartbeat detection derives the heartbeat frquency from ultrasonic signals reflected from the heart and frequency-shifted due to the Doppler effect. The circuit allows for the automatic determination of the distance between the heart and an ultrasonic transducer located on the body of the patient, so that the evaluation of the reflected ultrasonic signals can be limited to a small body range and spurious signals from other ranges can be suppressed. The circuit comprises at least two channels which are enabled by a transmitting/receiving control circuit during receiving intervals for receiving and further processing the reflected ultrasonic signals. The receiving intervals of the different channels are time shifted toward one another so that the respectively received ultrasonic signals originate from different depth ranges within the body. A comparison circuit compares the strengths of the signals corresponding to the heartbeat during each heartbeat period in the individual channels, and thus derives a gradient which indicates the direction in which the receiving intervals or transmit windows are to be shifted during the subsequent heartbeat period in order to localize the heart.

8 Claims, 8 Drawing Sheets

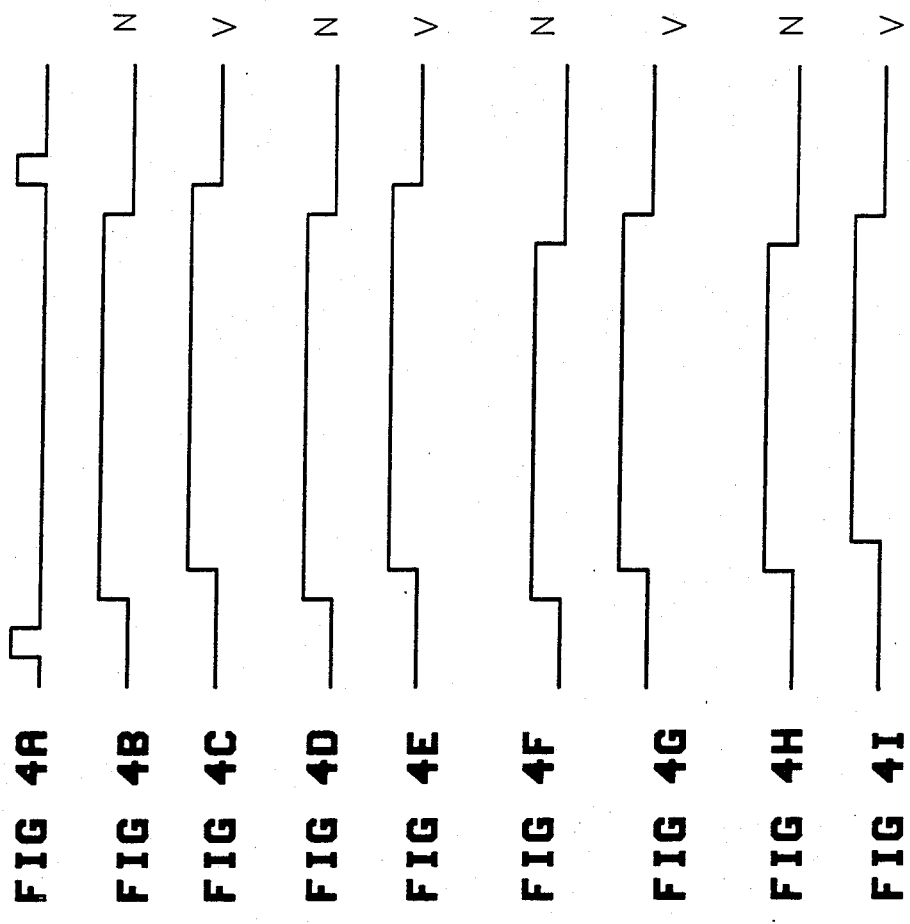

N

V

N

V

N

V

N

V

N

V

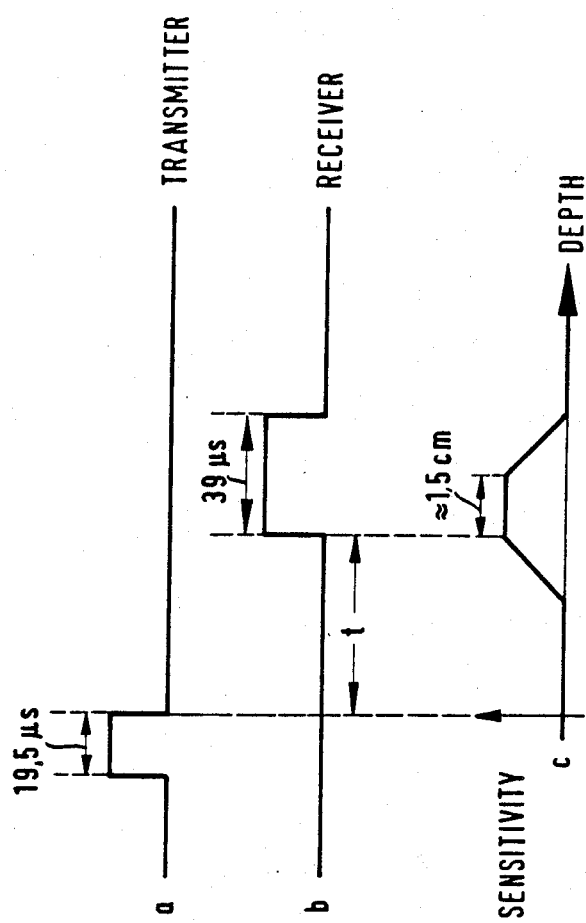

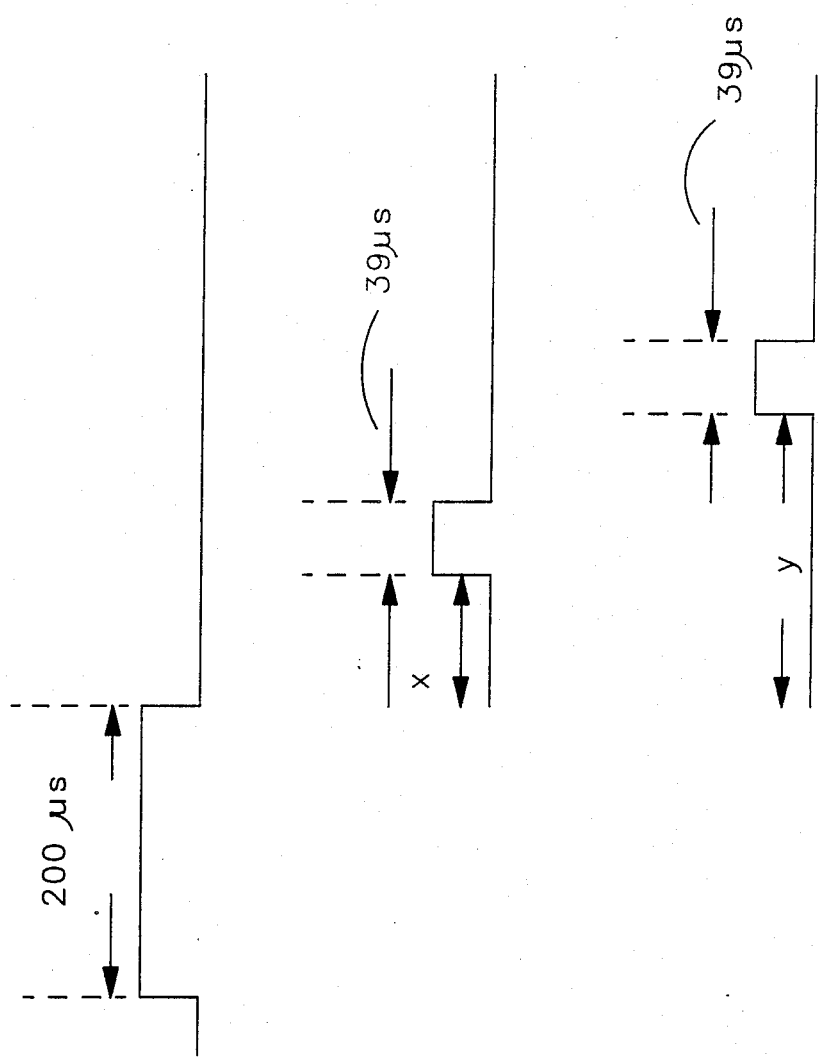

CIRCUITRY FOR HEARTBEAT

CROSS REFERENCE TO RELATED APPLICATION

This application is a continuation of application Ser. No. 07/148,205, filed Jan. 19, 1988 now abandoned, which is continuation of application Ser. No. 07/085,267, filed Aug. 11, 1987 now abandoned, which is a continuation of application Ser. No. 867,346 filed May 23, 1986, now abandoned.

BACKGROUND OF THE INVENTION

The invention relates to a circuitry for heartbeat detection, particularly for detecting fetal heartbeat.

A circuit is described in U.S. Pat. No. 4,143,650 for heartbeat detection. The circuit is connected to a transmitter and to a receiver for ultrasound which are placed on the body of a pregnant woman. The ultrasonic signals of a specific carrier frequency emitted by the transmitter are reflected by structures within the body, and the reflected signals which are received by the receiver are converted into electrical signals which are evaluated in the connected circuit. Due to the Doppler effect, ultrasonic signals which are reflected by moving structures, for example, the fetal heart, are frequency shifted relative to the transmitted signals. The frequency-shifted echo signals are demodulated in the connected circuit so that from the velocity of the heartbeat motion a respective Doppler signal results from which the frequency of the fetal heartbeat can be derived.

In this known circuit, various depth ranges can be adjusted by taking into consideration the speed of propagation of the ultrasonic signal within the body of the pregnant woman in such a way that respectively only echo signals originating from this respective depth range are evaluated. In this way, spurious signals originating from moving layers or organs located in a range other than the selected depth range can be suppressed. The depth range is thereby adjusted by the operator according to the presumed depth of the fetal heart.

If the operator does not have any knowledge as to the momentary depth of the fetal heart, the depth range would have to be adjusted in a time consuming and tedious test procedure in which in subsequent search steps varying depth zones would have to be adjusted to finally select the adjustment which in the estimation of the operator would result in the best measuring signal. In addition to the great amount of time required for the adjustment of the correct depth, another disadvantage would be that during the adjustment process the heartbeat signal may be lost if a depth range is selected which does not contain the fetal heart.

Furthermore, due to rather frequently occurring position changes of the fetus, the fetal heart may be moving out of the once selected depth range during the examination so that a dependable measurement of the heartbeat frequency is no longer possible. Since the operator does not have any knowledge as to the direction in which the fetal heart has moved during such a position change, new adjustment of the depth range would in this case also necessitate the tedious test procedure already mentioned.

BRIEF SUMMARY OF THE INVENTION

It is the object of the present invention to develop a circuit which, even with a moving fetus, will allow for a more rapid and dependable adjustment of the depth range.

According to an underlying principle of the present invention, the adjustment of the depth range can be accelerated through derivation of a tendency indication which indicates the direction in which the fetal heart is located. For that, at least two receiving channels are provided for the evaluation of the reflected ultrasonic signals. The channels are respectively enabled during different time intervals for deriving the Doppler signal corresponding to the heartbeat, so that the signals evaluated in the two channels correspond to echo signals from different depth ranges. In each channel, the strengths of the Doppler signals which correspond to the heartbeat are derived in subsequent heartbeat periods. The direction in which the fetal heart is located can be immediately determined from the strengths of the Doppler signals in different channels corresponding to different depth ranges during a heartbeat period.

In the subsequent heartbeat period, the depth ranges are shifted in the direction determined in the preceding heartbeat period by adjusting the relative timing of the emitted ultrasound impulses and the receiving windows in the receiving channels, i.e. by adjusting the duration of and the time spacing between the transmit pulses and the receiving windows. If necessary, the depth ranges are decreased by shortening either the transmit pulse or the receiving window. In this way, the depth of the fetal heart is determined in a few steps and the examined depth range is adjusted correspondingly so that the portion of spurious signals in the received echo signals is substantially reduced. The depth ranges respectively examined in a search step overlap so that, during the search procedure, there is always one evaluation signal available for determining the heartbeat and always one usable direction indication for the depth of the heart.

The strength of the Doppler signals in the different channels can be derived in various ways, for example, from the amplitude of the envelope signal of the demodulated echo signals or from the auto-correlation of the envelope curve.

The invention provides the additional advantage that long-term examinations of the fetal heartbeat can be carried out without an operator being present to adjust the depth range when the fetus changes location.

In accordance with the invention, the depth of the fetal heart can be continually determined during measurement and the depth range adjusted accordingly by adjusting the transmitreceive timing so that, even during movement of the fetus, optimal signal quality can always be maintained.

Further advantageous embodiments of the invention are also described.

One exemplary embodiment of the invention is explained with reference to the drawings. In this embodiment, the depth range is adjusted by varying the duration of the receiving windows. It is understood, however, that the depth selection according to the invention can also be performed by varying the duration of the transmit pulse and maintaining the duration of the receiving window at a constant value or by varying both the duration of the transmit pulse and the receiving window.

BRIEF DESCRIPTION OF THE DRAWINGS

FIGS. 4A to 4I illustrate the time sequence of control signals occurring during operation of the arrangement in accordance with FIG. 2;

FIGS. 7A to 7C illustrate the time sequence of control signals for the ultrasonic transmitter and for the ultrasonic receiver as well as the resulting sensitivity in the arrangement in accordance with FIG. 2 after completion of the search procedure; and FIG. 8 illustrates the operation of the apparatus of this invention in such manner that the duration of the transmitted pulse is varied and the respective durations of the windows during which the processing and comparison channels are open so as to pass signals remains constant.

DETAILED DESCRIPTION OF THE INVENTION

Figure 1:
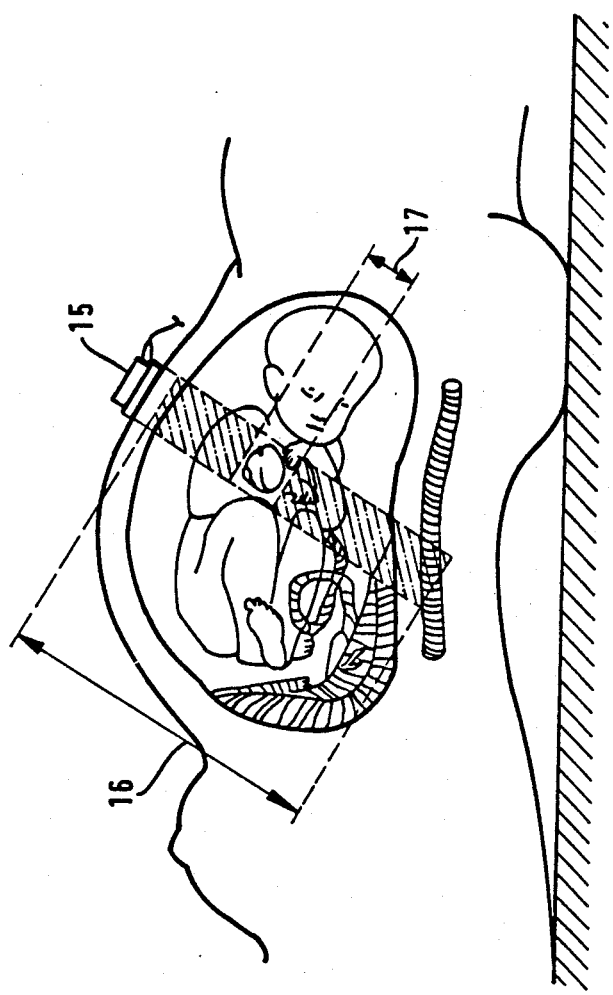
FIG. 1 is a schematic layout of an ultrasonic transducer on the abdomen of a pregnant woman and the location of the fetal heart to be examined.

In accordance with FIG. 1, an ultrasonic transducer 15 is placed on the abdomen of a pregnant woman for measuring the fetal heartbeat, said transducer transmitting an ultrasonic beam in the direction of the fetal heart. The ultrasonic beam is being reflected on various layers in the body of the pregnant woman and the child, for example, from the fetal heart.

While in known assemblies for measuring heartbeat, ultrasonic signals from the entire zone 16 or in a fixed zone within the body of the pregnant woman as adjusted by the operator are received and transmitted, the invention allows the automatic limitation of the area to be examined to region 17 of the fetal heart.

Figure 2:
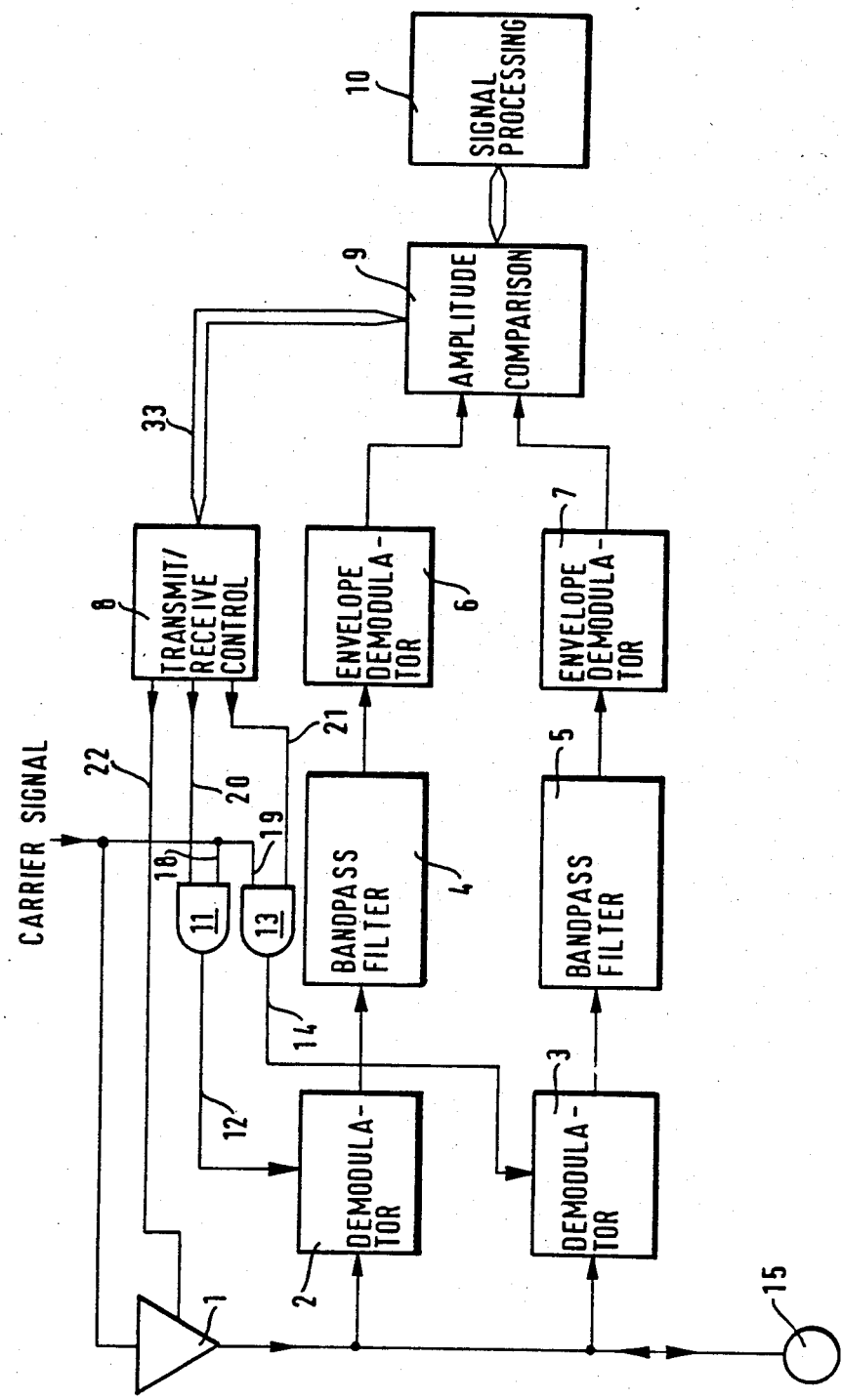
FIG. 2 is a schematic block diagram of an exemplary embodiment of the invention.

In accordance with FIG. 2, the circuit in accordance with the invention is connectable to an ultrasonic transducer 15 which may contain one or a plurality of piezoelectric crystals and which is excited by a drive circuit 1 for transmission of ultrasonic impulses. For the performance of a fetal heart examination, the transducer 15 is placed on the body of the pregnant woman so that ultrasonic signals of a high frequency, hereinafter referred to as "carrier signals", can enter the interior of the body. The carrier signals reflected by various layers within the body, including the signals reflected by the fetal heart, are received by an ultrasonic receiver located outside on the abdomen of the pregnant woman and are converted into electrical output signals. The carrier signals reflected by the beating fetal heart are frequency shifted due to the Doppler effect, and are coupled to means for deriving a signal corresponding to the heartbeat. The signal corresponding to the fetal heartbeat thereby generally results from the heart muscle, heart valve and associated blood flow movement of the fetus. The signal containing the information regarding the heartbeat, however, represents only a very small portion of the entire reflected signal, in which reflection signals of not moving or only weakly moving separate surfaces with respective frequency shifts form the main portion.

Preferably the same crystal is utilized as receiver which is also used as ultrasonic source. In this case, this transmitting/receiving crystal is being excited during subsequent transmitting/receiving periods in such a way that, during a first portion of a period, it operates as a transmitter for ultrasonic waves and, during the second portion, as a receiver. The ultrasonic transducer 15 in the shown embodiment is used for transmitting as well as receiving ultrasonic signals, but it would also be possible to use different crystals as transmitter and receiver.

The electric output signals of the ultrasonic receiver 15 are applied to two signal processing channels, hereinafter referred to as "processing channel" and "comparison channel". Since the two channels are substantially identical regarding the circuit configuration, only the processing channel is explained in detail. The output signal of the ultrasonic transducer 15 is applied to a demodulator 2 in the processing channel, that generates signals with frequency components which correspond to the difference between the frequency of the carrier signal and the Doppler shifted reflected ultrasonic signals.

For the generation of these Doppler signals, a pulsed carrier signal is applied to another input of the demodulator 2 via a line 12. The latter carrier signal has the same fundamental frequency as the transmitted carrier signal and is mixed with the output signals of the ultrasonic transducer 15 in the demodulator 2. The pulsed carrier signal on the lead 12 is controlled by a transmitting/receiving control circuit 8 by way of a gate circuit 11 in such a way that the Doppler signal is only generated during a selectable time interval. Details of the time sequence of this control are explained further later in this document. The gate circuit 11 is preferably designed as an AND gate.

A bandpass filter 4 is connected with the output of the demodulator 2, said bandpass filter only allowing passage of such signals whose frequencies lie in approximately the frequency range expected for the Doppler signals. At a carrier frequency of the ultrasonic signals of 1 MHz, for example, a bandpass filter with cut-off frequencies of 100 Hz and 475 Hz can be utilized. The output signal of the bandpass filter 4 is applied to an envelope demodulator 6 for the generation of an envelope signal whose signal curve corresponds to the respective Doppler signal. The envelope of the Doppler signals substantially corresponds to the intensity variation of the echo signals which are frequency shifted due to fetal heart beat movement, so that the peak values of the output signal of the envelope demodulator occur in rhythm with the fetal heartbeat.

The comparison channel also connected with the ultrasonic transducer 15 comprises a demodulator 3, a bandpass filter 5 and an envelope demodulator 7 which substantially correspond to the elements of the processing channel. On a line 14, the carrier signal for the generation of the Doppler signal is applied to demodulator 3. The time interval, however, during which the carrier signal is applied differs from the respective time interval in the processing channel.

The amplitudes of the envelope signals in the processing channel and in the comparison channel are subsequently compared to one another in an amplitude comparator circuit 9 in order to generate an output signal which is applied to the transmitter/receiver control circuit 8 which depends on this signal to control the application of the carrier frequency signals on the lines 12 and 14 to demodulators 2 and 3 respectively. The amplitude comparison may be carried out by way of an analog circuit, but preferably it is carried out digitally whereby the envelope signals in the processing channel and in the comparison channel are previously digitized with the aid of analog/digital converters (not shown). In case of digital signal processing, preferably a microprocessor is used for the amplitude comparison and for the generation of a respective control signal which is applied to the transmitter/receiver control circuit 8 on a line 33.

In a signal processing unit 10, the period or the frequency of the fetal heartbeat is determined from the time interval between two peak values of the (possibly digitized) output signal of one of the envelope demodulators.

In the following, the control of the application of the carrier signals by the transmitter/receiver control circuit 8 to demodulators 2 and 3 in the processing channel and the comparison channel respectively is explained in more detail:

The transmitter/receiver control circuit 8 controls the transmitter drive circuit 1 for the ultrasonic transducer 15 and the demodulators 2 and 3 such that in respectively one transmit/receive period during a first time interval the ultrasonic transmitter and during a subsequent time interval the demodulators are active. For that, the carrier signal is applied on a line 18 to an AND gate 11 connected with its output to the demodulator 2 and, on a line 19, to an AND gate 13 connected with its output to the demodulator 3. The AND gates 11 and 13 are respectively enabled for the passage of the carrier signals by a first enable signal on a line 20 and by a second enable signal on a line 21, said enable signals being respectively generated by the transmitter/receiver control circuit 8. When the first and the second enable signals are applied to the AND gates 11 and 13, the carrier signal reaches demodulators 2 and 3 respectively so that the respective Doppler signals can be detected. Furthermore, the transmitter/receiver control circuit 8 activates the driver circuit 1 for the ultrasonic transducer 15 through a third enable signal on a line 22 such that, during a predetermined time interval at the beginning of each transmit/receive period, ultrasonic pulses are transmitted.

Figure 3:
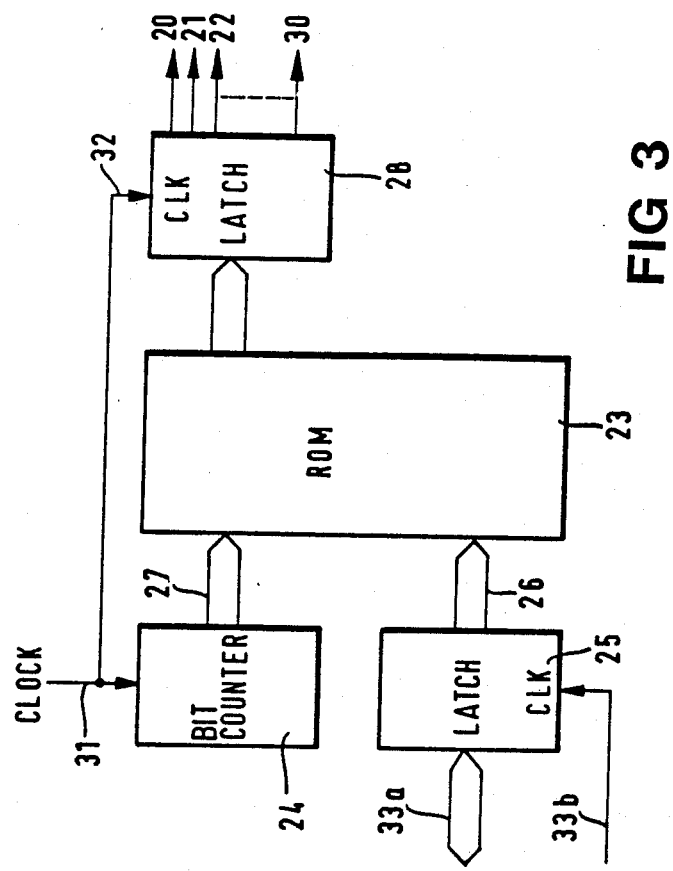
FIG. 3 is a circuit for the generation of control signals for the ultrasound transmitter and for the receiving circuits in an arrangement in accordance with the invention.

In FIG. 3, an example for a transmitter/receiver control circuit 8 is explained in more detail. In a read-only memory (ROM) 23 a plurality of data words are stored whose individual data bits are used for the activation of the ultrasonic transmitter 1, 15 and the demodulators 2 and 3 in the processing and the comparison channels respectively. When using a 4k×8 ROM, the highest address bits are addressed for depth selection in accordance with the respectively newly to be adjusted receiving windows by a microprocessor (not shown) via bus lines 33a and 33b connected to the microprocessor, a latch 25 and the address inputs 26, while the lower four bits are addressed by a counter 24 via the address inputs 27 and control the respective time sequence. If, in accordance with the shown exemplary embodiment, a 4-bit counter is used, a new data word with a length of 8 bits is being read from the ROM via a latch 28 at each new count. The serial data flowing on outputs 22, 20 and 21 respectively activate the drive circuit 1 and control the application of carrier waves via the leads 12 and 14 to the demodulator 2 in the processing channel and the demodulator 3 in the comparison channel respectively. The remaining five data lines (for example, line 30) can, if need be, be used for additional tasks, i.e., display controls. The clock input of latch 25 is connected with the control bus of the microprocessor via line 33b and a clock signal with a frequency of 51.2 kHZ is applied to the counter 24 and latch 28 on lines 31 and 32 respectively. With a 4-bit counter, the transmit/receive cycle is thus divided into sixteen time intervals. For a duration of the transmit/receive cycle of 312.5 microseconds, this results in individual time ranges of 19.5 microseconds, each of which corresponds to a depth resolution of approximately 1.5 centimeters. Therefore, the examined depth ranges in the processing channel and the comparison channel can be independently adjusted by control of the microprocessor in steps of approximately 1.5 cm (or a plurality thereof).

The time sequence of the signals for activating the drive circuit 1 and the demodulators 2 and 3 is shown by way of an example in FIGS. 4A to 4I. FIG. 4A shows the pulses for excitation of the drive circuit 1. In this exemplary embodiment, they occur with a repetition frequency of 3.2 kHz and with a duration of 19.5 microseconds. FIGS. 4B to 4I show four search steps for locating the depth of the fetal heart, whereby each search step is carried out during a different heartbeat period. The control signals for the processing channel are marked with an N, and the control signals for the comparison circuit with a V. A leading edge of the control signals corresponds to the start of activation, and a trailing edge corresponds to the end of activation of the respective demodulator. In this way, respectively one receiving window is defined which, according to the speed of propagation of the carrier signals, corresponds to a specific depth range in the examined body. Thereby the left side in the shown time sequence corresponds to the upper limit of the examined portion of the body located near the ultrasonic transducer 15, and the right side corresponds to the lower limit of the examined range within the body of the pregnant woman.

In accordance with FIG. 4B, after decaying of a transmit pulse (after occurrence of the trailing edge of the control signal shown in FIG. 4A), the demodulator 2 in the processing channel is activated for a specific time interval which is, at most, as long as the time interval between two subsequent transmit pulses (in this example, 312.5–19.5 microseconds).

As shown in FIG. 4C, the demodulator 3 in the comparison channel is activated for a specific time interval after the activation of demodulator 2 in the processing channel, and is blocked a specific time interval after the end of activation of demodulator 2. The time windows during which the processing and comparison channels are being enabled for the generation of Doppler signals therefore overlap to a large extent. The amplitude comparison of the output signals of the envelope demodulators 6 and 7 directly provides a tendency indication for the direction in which the fetal heart is located, i.e., a gradient which indicates the subsequent direction of search.

In the present example, it is assumed that the amplitude of the envelope signal in the processing channel is larger than in the comparison channel. Therefore, in the subsequent search step (see FIGS. 4D and 4E) in a new heartbeat period, the time window for the processing channel is shortened on that side on which the time window for the comparison channel exceeds the time window for the processing channel. At the same time, in accordance with FIG. 4E, the time window for the comparison channel is shortened by the same amount as the window for the processing channel. If, for example, the amplitude of the envelope signal obtained in the processing channel is still larger than the amplitude of the envelope signal obtained in the comparison channel, the time window for the processing channel in the following search step (FIGS. 4F, 4G) is shortened on that side on which the time window for the comparison channel exceeds the time interval for the processing channel. The comparison window is also shortened on the same side by the same extent. As a result, window adjustments as shown in FIGS. 4F and 4G are obtained. With the assumption that the comparison channel now delivers a larger amplitude for the envelope signal than the processing channel, but not more than 25% larger, the window for the processing channel is shortened on that side which precedes the beginning of the window for the comparison channel. The window for the comparison channel is shortened on the same side and by the same amount as the window for the processing channel. The result is shown in FIGS. 4H and 4I.

In the example shown here, only the receiving windows are varied for reasons of clarity, while the transmitting window is constantly maintained at 19.5 microseconds. The signal quality could, however, be improved for each selected range in that the transmitting window would be enlarged and the receiving window shortened by the same amount.

By means of FIGS. 5A to 5K, a further example of the search procedure for locating the fetal heart is explained. This part of the search procedure is particularly used if the fetus in the womb is moving opposite to the present direction of search and thus the possibility exists of losing the heartbeat signal.

Figure 5A:
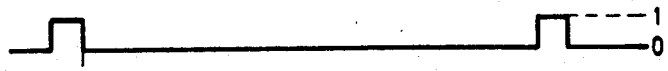
FIGS. 5A to 5K illustrate further examples of the control signals occurring during operation of an assembly in accordance with FIG. 2.

FIG. 5A shows the subsequent occurrence of two transmitting pulses.

Figure 5B:
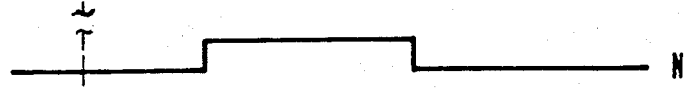
Figure 5C:
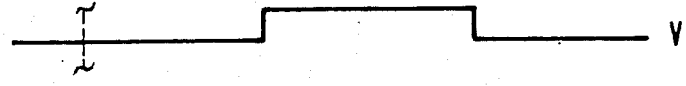
Figure 5D:
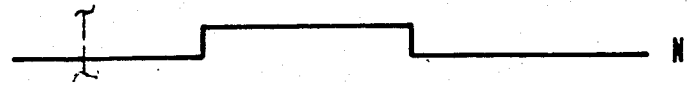
Figure 5E:
Figure 5F:
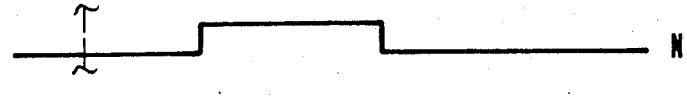
Figure 5G:
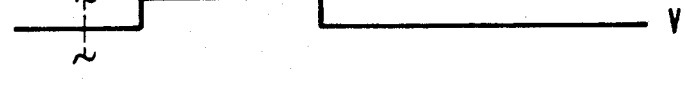
Figure 5H:
Figure 5I:
Figure 5J:
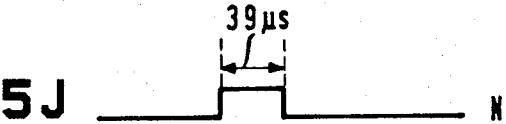
Figure 5K:
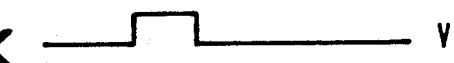

FIGS. 5B and 5C show the window for the processing channel and for the comparison channel, respectively, after some prior search steps (not shown). It is assumed that neither of the receiving windows is located at the borders of the search zone. The lengths of the windows In the timing diagram of FIG. 5A, the search zone corresponds to an interval starting at a predetermined time after the trailing edge of the transmit pulse and extending up to the leading edge of the next transmit pulse. The corresponding depth range is illustrated in FIG. 1 by the shaded area 16. In the examples shown in FIGS. 5B and 5C, it is further assumed that the envelope signal in the processing channel has a layer amplitude than the one in the comparison channel, and that in the previous search steps (not shown) the comparison window has always been on the same side of the processing window as in FIGS. 5B and 5C. The window for the processing channel remains in the previous position in the subsequent search step shown in FIG. 5D, whereas the window for the comparison channel now extends beyond the other side of the processing channel window. The lengths of the windows thereby remain unchanged. In the example shown in FIGS. 5D and 5E, it is assumed that the Doppler signal in the comparison channel is stronger than the one in the processing channel, but not more than 25% stronger. Consequently, the time windows in the processing channel and in the comparison channel are shortened in the next step as shown in FIGS. 5F and 5G on the side which is opposite to the side where the window with the larger signal protrudes beyond the window with the weaker signal. FIGS. 5H and 5I show a search step which occurs when the signal in the comparison channel suddenly becomes much larger than the one in the processing channel e.g. by a factor of 1.25, due to a sudden change in the location of the heart. In the search step as shown, the sizes of the windows are maintained, but the windows as a whole are displaced in the direction of displacement of the comparison window. Decreases of the window occur until a minimal predetermined window width is obtained as shown in FIGS. 5J and 5K, which allows optimum depth selection. A displacement of the windows continues to be possible.

Figure 6:
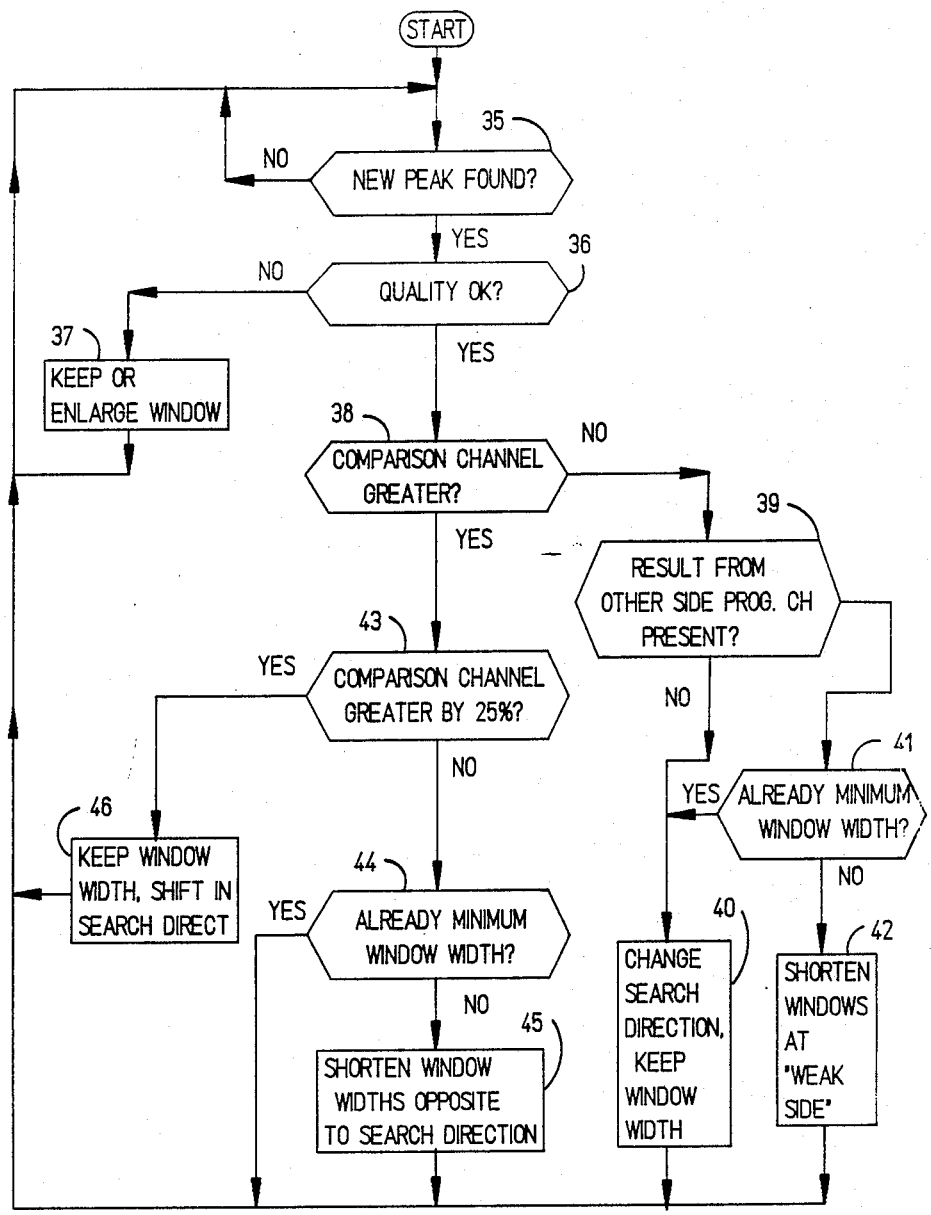
FIG. 6 is a flow diagram showing the search procedure for determining the depth of the fetal heart.

FIG. 6 explains the search process for localizing the depth of the fetal heart by means of a flow diagram. The steps described in the following can thereby be program-controlled by means of a microprocessor.

Initially, it is checked whether a new peak value which could correspond to a heartbeat signal has occurred in the processing channel, block 35. If such a peak value is determined, it is subsequently checked whether the signal quality is sufficient so as to allow for further processing, block 36. A criterium for signal quality can, for example, be derived from the auto-correlation of the output signal of the envelope demodulator. The quality determines whether the receiving window is maintained or enlarged, block 37. Then the process starts anew. With this procedure, "lost" signal sources are found again or a new placement of the ultrasonic transducer 15 can be taken into consideration. Before continuing with the description of FIG. 6, the terms "search direction" and "weak side" which are used in the flow chart are defined: "Search direction" is the direction in which the window of the channel (processing channel or comparison channel) having the stronger signal protrudes beyond the window having the weaker signal. The "weak side" is the side opposite to the search direction. In the unlikely event that the amplitudes of the envelopes on each channel should be identical, the "weak side" is the side on which the comparison window protrudes beyond the window for the processing channel.

At sufficient signal quality, the amplitude of the envelope signal in the comparison channel is checked to see if it is larger than the envelope signal in the processing channel block 38. If it is not, a check is made to see if a result from the other side of the processing channel is present, block 39, that means it is checked if a result is present from a previous step in which the comparison window has protruded beyond the processing window on the side opposite to the side at which the comparison window protrudes beyond the processing window in the present step. If this has not occurred during a previous search step the instruction according to block 40 is carried out, i.e., the processing window remains at its location and the comparison window is shifted to the other side of the processing window with the widths of the comparison window and of the processing window remaining unchanged. Then the process starts at the beginning with a check if a new peak value has been found. If a comparison with the other side of the processing window, block 39, has already been carried out, it first of all is checked whether the minimal window width has already been reached. If so, the search direction is also hanged, block 40, and the process starts at the beginning. If no, the windows are decreased on the weak side, block 42, and the process starts at the beginning (compare FIGS. 5F and 5G). A special case is the situation where the processing window is located at the border of the search zone as in FIG. 4B. In this case, the answer to the question in block 39 "RESULT FROM OTHER SIDE OF PROCESSING CHANNEL PRESENT" is assumed to be "YES" in accordance with the transition from FIGS. 4B and 4C to FIGS. 4D and 4E.

If the Doppler signal in the comparison channel is larger than the one in the processing channel, it is then checked, block 43, whether the signal in the comparison channel is significantly larger than the signal in the processing channel. In this example, the criterion is whether the signal in the comparison channel exceeds the signal in the processing channel by more than 25%. If this is so, the window widths are maintained and the windows are displaced in the search direction (compare FIGS. 5F-5G with FIGS. 5H-5I). If the signal in the comparison channel deviates from the signal in the processing channel by less than 25%, the process is started anew in case the minimum window width has already been reached, as indicated by block 44. If the minimum window width has not been reached, the weak sides of the windows, i.e. the sides opposite to the direction of search decreased and the process is started anew.

FIG. 7C shows the sensitivity range of the heartbeat measurement for the adjusted state after locating the depth of the fetal heart. The transmitting pulse shown in FIG. 7A has a length of 19.5 microseconds and the receiving window in an adjusted state is opened for a duration of 39 microseconds in accordance with FIG. 7B. FIG. 7C shows the sensitivity resulting from this receiving window in dependence of the depth. The sensitivity is substantially constant over a range of 1.5 cm and decreases linearly at the edges.

It is understood that the described procedure for limiting the sensitivity range to the fetal heart is not the only one possible. It is important that at least two channels be provided which, due to the different times of activation, deliver Doppler signals from various depth ranges so that a gradient for the direction of search for the subsequent search step can be derived thus permitting optimum adjustment of the position of the processing window with respect to the fetal heart.

The manner in which the apparatus of FIG. 2 operates with a transmitted pulse of constant duration and with the windows for the processing and comparison channels of varying duration has been described, but the same apparatus can be made to operate with transmitted pulses of varying duration and the windows for the channels of constant duration, as illustrated in FIG. 8. In either case, means are provided for obtaining reflections from different but overlapped depth ranges. Initially, the transmitted pulse has a much longer duration, e.g., 200 microseconds rather than 39 microseconds. The processing channel is opened so as to pass signals x microseconds after the trailing edge of the transmitted pulse and remain open for a relatively short time, such as 39 microseconds. The comparison channel is opened so as to pass signals y microseconds after the trailing edge of the transmitted pulse and remain open for a relatively short time, e.g., 39 microseconds. At least some of the reflections of the transmitted pulse from the fetal heart will pass through at least one of the channels, and the amplitude comparison means 9 will cause the windows for the two channels to move in the direction of the window having the stronger signal and preferably shorten the transmitted pulse. Should the depth of the location of the fetal heart change, the ratio of the amplitudes of the Doppler signals in the two channels will be reduced and the duration of the transmitted pulse increased so as to ensure that reflections of at least a portion of the transmitted pulse will pass through at least one of the channels. The apparatus would then operate as just described so that the window for the processing channel straddles the depth range of the fetal heart.

It will be obvious to one skilled in the art that a combination of the two methods of operation could be used in which the duration of the transmitted pulse and the durations of the windows for the processing and comparison channels are all changed.

In any of these methods of operation, means are provided for respectively applying signals from displaced depth ranges to the processing and comparison channels, means are provided for determining the relative amplitudes of Doppler shift signals in the channels, and means responsive to the relative amplitudes are provided for opening the processing channel for a time during which reflections are being received from the fetal heart.

What is claimed is:

1. Apparatus for detecting the location of a fetal heartbeat, comprising
    transmitter means for launching ultrasound pulses of a given carrier frequency,
    transducing means for converting reflections of launched ultrasound pulses into corresponding electrical waves,
    a normally inoperative processing channel having an input coupled to said transducing means, said processing channel having means for providing a first signal at an output thereof that represents the strength of Doppler signals applied to the input of said channel from said transducing means,
    a normally inoperative comparison channel having an input coupled to said transducing means, said comparison channel having means for providing a second signal at an output thereof that corresponds to the strength of Doppler signals applied to the input of said channel from said transducing means,
    control means for making said processing channel operative to produce said first signal during a first time window after a pulse is launched by said transmitting means and for making said comparison channel operative to produce said second signal during a second time window after said pulse is launched by said transmitting means, said time windows being displaced from each other so that the signals respectively passing through said channels are from different but overlapping depth ranges,
    a comparison means coupled to said channels for providing at an output thereof a signal indicating which channel has the stronger Doppler signal, thus indicating which depth range gives a better match with the location of the fetal heart, and
    means responsive to the comparison means output signal for stepwise shortening of the depth ranges corresponding to the time windows of the processing and comparison channels down to predetermined minimum depth ranges such that after a number of steps an optimum match of the location of the fetal heart with the depth range corresponding to the processing channel is achieved even if the fetal heart changes its location in depth.

2. Apparatus for locating a depth range to which a processing channel is responsive comprising:

transmitter means for launching ultrasound pulses of a given carrier frequency, transducing means for converting reflections of launched ultrasound pulses into corresponding electrical waves, a processing channel having an input coupled to said transducing means, said processing channel having means for detecting Doppler signals from a moving object within said depth range contained in said electrical waves and means for providing a first signal at an output thereof that represents the maximum amplitude of said Doppler signals, a comparison channel having an input coupled to said transducer means, said comparison channel having means for detecting Doppler signals from a moving object within said depth range contained in said electrical waves and means for providing a second signal at an output thereof that represents the maximum amplitude of said Doppler signals, control means for enabling said processing channel to produce said first signal in response to said Doppler signals occurring only during a first time or depth window and for enabling said processing channel to produce said second signal in response to said Doppler signals occurring only during a second time or depth window, said time windows being overlapped but including different periods of time, a comparison means coupled to said channels for providing a comparison signal indicating whether or not said second signal has a greater amplitude than said first signal, and said control means being responsive to said comparison signal for time adjusting at least one of said windows on its weak side regardless of which of said first and second signals is the larger.

3. Apparatus as set forth in claim 2 wherein said control means has means for keeping the duration of the transmitted pulses constant and varies the duration of said windows.

4. Apparatus as set forth in claim 2 wherein said control means has means for varying the duration of the transmitted pulses as well as the duration of the windows.

5. Apparatus as set forth in claim 2 wherein said control means has means for keeping the widths of the windows the same and for shifting said second or comparison window to said second or other side of said first or processing window if the comparison signal indicates that said second signal is not greater than said first signal and if said comparison means has not provided a oomparison signal with the comparison window on the one side of said processing window or if it has given such a comparison signal and the windows are at a given minimum width.

6. Apparatus as set forth in claim 2 wherein said control means has means for shifting both windows in a direction of search if said comparison means indicates that said first signal is greater than said second signal by more than a given amount.

7. Apparatus as set forth in claim 2 wherein said control means has means for preventing further shortening of said windows if their widths have reached a given minimum value.

8. Apparatus for locating a depth range to which a processing channel is responsive comprising:

transmitter means for launching ultrasound pulses of a given carrier frequency, transducing means for converting reflections of launched ultrasound pulses into corresponding electrical waves, a processing channel having an input coupled to said transducing means, said processing channel having means for detecting Doppler signals from a moving object within said depth range contained in said electrical waves and means for providing a first signal at an output thereof that represents the maximum amplitude of said Doppler signals, a comparison channel having an input coupled to said transducer means, said comparison channel having means for detecting Doppler signals from a moving object within said depth range contained in said electrical waves and means for providing a second signal at an output thereof that represents the maximum amplitude of said Doppler signals, control means for enabling said processing channel to produce said first signal in response to said Doppler signals occurring only during a first time or depth window and for enabling said processing channel to produce said second signal in response to said Doppler signals occurring only during a second time or depth window, said time windows being overlapped but including different periods of time, a comparison means coupled to said channels for providing a comparison signal indicating whether or not said second signal has a greater amplitude than said first signal, and said control means being responsive to said comparison signal for shifting said first and second windows in the direction of the window having the stronger signal, and for reducing the duration of the next transmitted pulse.

* * * * *